US008834862B2

(12) United States Patent
Lotan et al.

(10) Patent No.: US 8,834,862 B2
(45) Date of Patent: Sep. 16, 2014

(54) METHODS, COMPOSITIONS AND DEVICES UTILIZING STINGING CELLS/CAPSULES FOR CONDITIONING A TISSUE PRIOR TO DELIVERY OF AN ACTIVE AGENT

(75) Inventors: Tamar Lotan, Jordan Valley (IL); Shimon Eckhouse, Haifa (IL)

(73) Assignee: NanoCyte Inc., Wilmington, DE (US)

( * ) Notice: Subject to any disclaimer, the term of this patent is extended or adjusted under 35 U.S.C. 154(b) by 0 days.

(21) Appl. No.: 11/108,662

(22) Filed: Apr. 19, 2005

(65) Prior Publication Data

US 2006/0234203 A1 Oct. 19, 2006

(51) Int. Cl.
*A01N 63/00* (2006.01)
*C12N 5/00* (2006.01)

(52) U.S. Cl.
USPC ......... 424/93.21; 435/1.1; 435/325; 424/520; 424/400; 424/443; 424/480

(58) Field of Classification Search
CPC .. A61K 35/614; A61K 2300/00; A61K 38/00
See application file for complete search history.

(56) References Cited

U.S. PATENT DOCUMENTS

| | | |
|---|---|---|
| 3,321,188 A | 5/1967 | Unger |
| 3,791,932 A | 2/1974 | Schuurs et al. |
| 3,839,153 A | 10/1974 | Schuurs et al. |
| 3,850,578 A | 11/1974 | Mc Connell |
| 3,850,752 A | 11/1974 | Schuurs et al. |
| 3,853,987 A | 12/1974 | Dreyer |
| 3,867,517 A | 2/1975 | Ling |
| 3,879,262 A | 4/1975 | Schuurs et al. |
| 3,901,654 A | 8/1975 | Gross |
| 3,935,074 A | 1/1976 | Rubenstein et al. |
| 3,984,533 A | 10/1976 | Uzgiris |
| 3,996,345 A | 12/1976 | Ullman et al. |
| 4,034,074 A | 7/1977 | Miles |
| 4,098,876 A | 7/1978 | Piasio et al. |
| 4,666,828 A | 5/1987 | Gusella |
| 4,801,531 A | 1/1989 | Frossard |
| 4,879,219 A | 11/1989 | Wands et al. |
| 5,011,771 A | 4/1991 | Bellet et al. |
| 5,073,488 A | 12/1991 | Matner et al. |
| 5,162,378 A | 11/1992 | Guthauser |
| 5,192,659 A | 3/1993 | Simons |
| 5,272,057 A | 12/1993 | Smulson et al. |
| 5,281,521 A | 1/1994 | Trojanowski et al. |
| 5,362,442 A | 11/1994 | Kent |
| 5,641,508 A | 6/1997 | Li et al. |
| 5,885,211 A | 3/1999 | Eppstein et al. |
| 5,885,260 A | 3/1999 | Mehl, Sr. et al. |
| 6,019,967 A | 2/2000 | Breton et al. |
| 6,022,316 A | 2/2000 | Eppstein et al. |
| 6,132,747 A | 10/2000 | Lotan |
| 6,338,837 B1 | 1/2002 | Lotan |
| 6,406,709 B1 | 6/2002 | Lotan |
| 6,416,960 B1 | 7/2002 | Bryan |
| 6,596,531 B2 | 7/2003 | Campbell et al. |
| 6,613,344 B2 | 9/2003 | Lotan et al. |
| 6,613,744 B2 | 9/2003 | Wozney et al. |
| 7,338,665 B2 | 3/2008 | Lotan et al. |
| 7,611,723 B2 | 11/2009 | Lotan et al. |
| 7,632,522 B2 | 12/2009 | Lotan et al. |
| 7,998,509 B2 | 8/2011 | Lotan et al. |
| 8,062,660 B2 | 11/2011 | Lotan et al. |
| 8,287,912 B2 | 10/2012 | Lotan et al. |
| 2002/0039592 A1 | 4/2002 | Lotan et al. |
| 2003/0189850 A1 | 10/2003 | Sasaki et al. |
| 2003/0202995 A1 | 10/2003 | Lotan et al. |
| 2004/0224013 A1 | 11/2004 | Lotan et al. |
| 2004/0235143 A1 | 11/2004 | Sasaki et al. |
| 2007/0160546 A1 | 7/2007 | Lotan et al. |
| 2010/0055058 A1 | 3/2010 | Lotan et al. |
| 2011/0070224 A1 | 3/2011 | Lotan et al. |
| 2011/0250245 A1 | 10/2011 | Lotan et al. |

FOREIGN PATENT DOCUMENTS

| | | |
|---|---|---|
| EP | 1519755 | 4/2005 |
| WO | WO 98/29134 | 9/1999 |
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 00/03758 | 1/2000 |
| WO | WO 00/04821 | 3/2000 |
| WO | WO 00/04832 | 3/2000 |
| WO | WO 00/15102 | 3/2000 |
| WO | WO 01/37778 | 5/2001 |
| WO | WO 02/26191 | 4/2002 |
| WO | WO 03/079967 | 2/2003 |
| WO | WO 2006/111960 | 10/2006 |

OTHER PUBLICATIONS

Holstein "An Ultrahigh-Speed Analysis of Exocytosis: Nematocyst Discharge", Science, 223(4638): 830-833, 1984.
Lotan et al. "Toxin Compartmentation and Delivery in the Cnidaria: The Nematocyst's Tubule as a Multiheaded Poisonous Arrow", The Journal of Experimental Zoology, 275(6): 444-451, 1996.
Weber "Nematocysts (Stinging Capsules of Cnidaria) as Donnan-Potential-Dominated Osmotic Systems", European Journal of Biochemistry, 184: 465-476, 1989.
Tardent "The Cnidarian Cnidocyte, a High-Tech Cellular Weaponry", BioEssays, 17(4): 351-362, 1995.
Anderson et al. "A Triploblast Origin for Myxozoa?", Nature, 392(6674): 346-347, 1998.
Godknecht et al. "Discharge and Mode of Action of the Tentacular Nematocysts of *Anemonia sulcata* (Antozoa: Cnidaria)", Marine Biology, 100: 83-92, 1988.
Heeger et al. "Protection of Human Skin Against Jellyfish (*Cyanea capillata*) Stings", Marine Biology, 113: 669-678, 1992. Abstract.
Koch "Spinalin, A New Glycine- and Histidine-Rich Protein in Spines of Hydra Aematocysts", Journal of Cell Science, 111: 1545-1554, 1998.
Lotan et al. "Delivery of a Nematocyst Toxin", Nature, 375(6531): 456, 1995.
Lubbock "Chemical Recognition and Nematocyte Exitation in a Sea Anemone", Journal of Experimental Biology, 83: 283-292, 1979.

(Continued)

*Primary Examiner* — Lora E Barnhart Driscoll

(57) ABSTRACT

Methods, compositions and devices utilizing stinging cells/capsules for conditioning a tissue prior to delivery of a pharmaceutical agent are described.

6 Claims, 4 Drawing Sheets
(2 of 4 Drawing Sheet(s) Filed in Color)

(56) References Cited

OTHER PUBLICATIONS

Siddall et al. "The Demise of a Phylum of Protists: Phylogeny of Myxozoa and Other Parasitic Cnidaria", Journal of Parasitology, 81(6): 961-967, 1995.
Thorington et al. "Control of Cnida Discharge: I. Evidence for Two Classes of Chemoreceptor", Biol. Bull., 174: 163-171, 1988.
Watson et al. "Cnidocyte Mechanoreceptors are Tuned to the Movements of Swimming Prey by Chemoreceptors", Science, 243: 1589-1591, 1989.
Lohmann et al. "Silencing of Developmental Genes in *Hydra*", Developmental Biology, 214: 211-214, 1999.
Westfall et al. "Ultrastructure of the Dinoflagellate Polykrikos. I. Development of the Nematocyst-Taeniocyst Complex and Morphology of the Site for Extrusion", Journal of Cell Science, 63: 245-261, 1983.
Kimball et al. "Efficacy of Jellyfish Sting Inhibitor in Preventing Jellyfish Stings in Normal Volunteers", Wilderness Environ. Med., 15(2): 102-108, 2004. Abstract.
Lotan et al. "Skin Protection Against Seabather's Eruption and Jellyfish Sting", American Academy of Dermatology, p. 172-173, 2002. Poster Abstract No. p. 458.
Sharp "RNAi and Double-Strand RNA", Genes & Development, 13: 139-141, 1999.
Wang et al. "Isolation and Characterization of a Mini-Collagen Gene Encoding a Nematocyst Capsule Protein From a Reef-Building Coral, *Acropora donei*", Gene, 152(2): 195-200, 1995. Abstract.
Miljovic et al. "GFP Expression in *Hydra*", International Workshop—Evangelische Akademie, Tutzing/Germany, 2001. Abstract.
Cikala et al. "Expression of GFP-Fusion Protein in *Hydra* to Investigate the Function of Genes Linked With Apoptosis", International Workshop—Evangelische Akademie, Tutzing/Germany, 2001.
Engel et al. "Atomic Force Microscopy: A Powerful Tool to Observe Biomolecules at Work", Trends in Cell Biology, 9:77-80, 1999.
Brennecke et al. "The Lack of a Stress Response in *Hydra oligactis* is Due to Reduced Hsp70 mRNA Stability", European Journal of Biochemistry, 255: 703-709, 1998.
Hidaka "Mechanism of Nematocyst Discharge and its Cellular Control", Advances in Comparative and Environment Physiology, 15(Chap.2): 45-76, 1993.
Tardent et al. "Morphology and Morphodynamics of the Stenotele Nematocyst of *Hydra attenuata* Pall. (Hydrozoa, Cnidaria)", Cell and Tissue Research, 224(2): 269-290, 1982.
Watson et al. "Receptors for N-Acetylated Sugars May Stimulate Adenylate Cyclase to Sensitize and Tune Mechanoreceptors Involved in Triggering Nematocyst Discharge", Experimental Cell Research, 198(1): 8-16, 1992.
Smothers et al. "Molecular Evidence That the Myxozoan Protists are Metazoans", Science, 265(5179): 1719-1721, 1994.
Ozbek et al. "A Switch in Disulfide Linkage During Minicollagen Assembly in *Hydra* Nematocysts", The EMBO Journal, 20(12): 3063-3073, 2001. Abstract.
Murate et al. "*Hydra* Regeneration From Recombinant Ectodermal and Endodermal Tissue—II. Differential Stability in the Ectodermal and Endodermal Epithelial Organization", Journal of Cell Science, 110: 1155-1164, 1997.
Fernandez-Alonso et al. "DNA Vaccination by Immersion and Ultrasound to Trout Viral Heamorrhagic Septicaemia Virus", Vaccine, 19: 3067-3075, 2001. Abstract.
Anderluh et al. "A Common Motif in Proparts of Cnidarian Toxins and Nematocyst Collagend and its Putative Role", Biochimica and Biophysica Acta, 1476: 372-376, 2000. Abstract.
Miljkovic et al. "Cnidarian and Bilaterian Promoters Can Direct GFP Expression in Transfected *Hydra*", Development Biology, 246: 377-390, 2002.
B?ttger et al. "GFP Expression in *Hydra*: Lessons From the Particle Gun", Development in Genes Evolution, 212: 302-305, 2002.
Hidaka et al. "Effects of Calkcium on the Mechanical Properties of the Capsule Wall of Isolated Nematocysts from *Calliactis polypus*", Comp. Biochem. Physiol., 107A(1): 31-36, 1994.
Bode "The Interstitial Cell Lineage of *Hydra*: A Stem Cell System That Arose Early in Evolution", Journal of Cell Science, 109: 1155-1164, 1996.
Stauffer et al. "Common Florida Injuries", Empulse, 8(3.2): 11-14, 2003.
Salleo et al. "Release of Free CA2+ From the Nematocysts of *Aiptasia mutabilis* During the Discharge", Physiology & Zoology, 61(3): 272-279, 1988.
Lubbock et al. "Removal of Bound Calcium From Nematocyst Contents Causes Discharge", Nature, 290(5806): 500-501, 1981.
Weber et al. "Some Physical and Chemical Properties of Purified Nematocysts of *Hydra attenuata* Pall. (Hydrozoa, Cnidaria)", Comparative Biochemistry and Physiology, 88B(3): 855-862, 1987.
Gerke et al. "The Spatial Distribution of Cations in Nematocytes of *Hydra vulgaris*", Hydrobiologia, 216/217: 661-669, 1991.
Watson et al., "Cnidocyte Mechanoreceptors are Tuned to the Movements of Swimming Prey by Chemoreceptors", Science, 243: 1589-1591, 1989.
Office Action Dated Jul. 7, 2008 From the Israeli Patent Office Re.: Application No. 155097.
Office Action Dated Jul. 20, 2007 From the Israeli Patent Office Re.: Application No. 155097.
Office Action Dated Jun. 20, 2007 From the Israeli Patent Office Re.: Application No. 1550967.
Official Action Dated Nov. 1, 2007 From the US Patent and Trademark Office Re.: U.S. Appl. No. 11/328,221.
Official Action Dated Oct. 4, 2007 From the US Patent and Trademark Office Re.: U.S. Appl. No. 10/507,692.
Official Action Dated Oct. 9, 2008 From the US Patent and Trademark Office Re.: U.S. Appl. No. 11/328,221.
Official Action Dated Dec. 15, 2006 From the US Patent and Trademark Office Re.: U.S. Appl. No. 11/328,221.
Official Action Dated Jul. 17, 2008 From the US Patent and Trademark Office Re.: U.S. Appl. No. 11/328,221.
Official Action Dated Nov. 17, 2008 From the US Patent and Trademark Office Re.: U.S. Appl. No. 10/507,692.
Official Action Dated Jan. 24, 2008 From the US Patent and Trademark Office Re.: U.S. Appl. No. 10/507,692.
Official Action Dated Mar. 30, 2007 From the US Patent and Trademark Office Re.: U.S. Appl. No. 11/328,221.
Communication Pursuant to Article 94(3) EPC Dated Dec. 17, 2008 From the European Patent Office Re.: Application No. 01976586.6.
International Search Report Dated Jun. 24, 2008 From the International Searching Authority Re.: Application No. PCT/IL2006/000465.
Supplementary Partial European Search Report Dated Feb. 6, 2007 From the European Patent Office Re.: Application No. 01976586.6.
Written Opinion Dated Jun. 24, 2008 From the International Searching Authority Re.: Application No. PCT/IL2006/000465.
International Preliminary Report on Patentability Dated May 18, 2007 From the International Bureau of WIPO Re.: Application No. PCT/IL2005/001127.
International Search Report Dated Jun. 22, 2006 From the International Searching Authority Re.: Application No. PCT/IL05/01127.
Office Action Dated Jun. 4, 2008 From the Israeli Patent Office Re.: Application No. 164191.
Office Action Dated Feb. 15, 2009 From the Israeli Patent and Trademark Office Re.: Application No. 155097 and its Translation Into English.
Official Action Dated Oct. 4, 2006 From the US Patent and Trademark Office Re.: U.S. Appl. No. 10/868,802.
Official Action Dated Jun. 6, 2006 From the US Patent and Trademark Office Re.: U.S. Appl. No. 10/981,522.
Official Action Dated Aug. 8, 2006 From the US Patent and Trademark Office Re.: U.S. Appl. No. 11/374,969.
Official Action Dated Aug. 9, 2007 From the US Patent and Trademark Office Re.: U.S. Appl. No. 11/374,969.
Official Action Dated Feb. 20, 2008 From the US Patent and Trademark Office Re.: U.S. Appl. No. 11/374,969.
Official Action Dated Sep. 20, 2007 From the US Patent and Trademark Office Re.: U.S. Appl. No. 10/981,522.
Official Action Dated Apr. 25, 2008 From the US Patent and Trademark Office Re.: U.S. Appl. No. 10/981,498.

(56) References Cited

OTHER PUBLICATIONS

Official Action Dated Jul. 26, 2007 From the US Patent and Trademark Office Re.: U.S. Appl. No. 10/981,498.
Official Action Dated Feb. 27, 2007 From the US Patent and Trademark Office Re.: U.S. Appl. No. 11/374,969.
Official Action Dated Mar. 27, 2009 From the US Patent and Trademark Office Re.: U.S. Appl. No. 10/507,692.
Official Action Dated Dec. 28, 2007 From the US Patent and Trademark Office Re.: U.S. Appl. No. 10/981,522.
Official Action Dated Jul. 29, 2008 From the US Patent and Trademark Office Re.: U.S. Appl. No. 11/374,969.
Official Action Dated Nov. 29, 2006 From the US Patent and Trademark Office Re.: U.S. Appl. No. 10/981,522.
Official Action Dated May 30, 2006 From the US Patent and Trademark Office Re.: U.S. Appl. No. 10/981,498.
Official Action Dated Nov. 30, 2006 From the US Patent and Trademark Office Re.: U.S. Appl. No. 10/981,498.
Written Opinion Dated Jun. 22, 2006 From the International Searching Authority Re.: Application No. PCT/IL05/01127.
International Preliminary Report on Patentability Dated Dec. 11, 2008 From the International Bureau of WIPO Re.: Application No. PCT/IL2006/000465.
Notice of Allowance Dated Aug. 6, 2009 From the US Patent and Trademark Office Re.: U.S. Appl. No. 11/328,221.
Notice of Allowance Dated Jun. 19, 2009 From the US Patent and Trademark Office Re.: U.S. Appl. No. 10/507,692.
Office Action Dated Feb. 16, 2010 From the US Patent and Trademark Office Re.: U.S. Appl. No. 11/374,969.
Office Action Dated Nov. 23, 2009 From the Israeli Patent Office Re.: Application No. 155097 and its Translation Into English.
Official Action Dated Apr. 13, 2009 From the US Patent and Trademark Office Re.: U.S. Appl. No. 11/328,221.
Response Dated Feb. 22, 2010 to Office Action of Nov. 23, 2009 From the Israeli Patent Office Re.: Application No. 155097.
Response Dated Feb. 26, 2010 to Office Action of Feb. 16, 2010 From the US Patent and Trademark Office Re.: U.S. Appl. No. 11/374,969.
Response Dated Dec. 30, 2009 to Office Action of Jun. 25, 2009 From the Israel Patent Office Re.: Application No. 164191.
Hiroshi et al. "Chemical Characterization of the Nematocyst Toxin From the Hawaiian Jellyfish *Carybdea alata*", Symposium on the Chemistry of Natural Products, Symposium Papers, 42: 391-396, 2000. Abstract.
Official Action Dated Jul. 3, 2012 From the US Patent and Trademark Office Re. U.S. Appl. No. 12/955,990.
Response Dated Jul. 14, 2010 to Official Action of Jun. 18, 2010 From the US Patent and Trademark Office Re.: U.S. Appl. No. 12/616,801.
Response Dated Aug. 10, 2010 to Phone Conversation of Aug. 1, 2010 With the Examiner Re. Application No. 155097.
Response Dated Aug. 10, 2010 to Phone Conversation of Aug. 1, 2010 With the Examiner Re. Application No. 199236.
Advisory Action Before the Filing of an Appeal Brief Dated Sep. 28, 2012 From the US Patent and Trademark Office Re. U.S. Appl. No. 12/955,990.
Communication Under Rule 71(3) EPC Dated Sep. 21, 2012 From the European Patent Office Re. Application No. 01976586.6.
Official Action Dated Nov. 8, 2012 From the US Patent and Trademark Office Re. U.S. Appl. No. 12/588,368.
Supplementary European Search Report and the European Search Opinion Dated Nov. 7, 2012 From the European Patent Office Re. Application No. 06728266.5.
Restriction Official Action Dated Dec. 2, 2011 From the US Patent and Trademark Office Re. U.S. Appl. No. 12/588,368.
Office Action Dated Feb. 27, 2011 From the Israeli Patent Office Re.: Application No. 164191 and its Translation Into English.
Official Action Dated Jun. 18, 2010 From the US Patent and Trademark Office Re.: U.S. Appl. No. 12/616,801.
Response Dated Jun. 14, 2011 to Official Action of Apr. 11, 2011 From the US Patent and Trademark Office Re.: U.S. Appl. No. 11/374,969.

Official Action Dated Apr. 6, 2009 From the US Patent and Trademark Office Re.: U.S. Appl. No. 11/374,969.
Response Dated Jun. 16, 2009 to Official Action of Apr. 6, 2009 From US Patent and Trademark Office Re.: U.S. Appl. No. 11/374,969.
"Skin, Hair, and Nails", http://web.archive.org/web.20030404084846/www.kidshealth.org/PageManager.jsp?dn=Kidshealth&lic=1&ps=107&cat_id-20090&article_set-20552, p. 1-7, 2003.
Office Action Dated Jun. 20, 2007 From the Israeli Patent Office Re.: Application No. 155097.
Official Action Dated Apr. 28, 2006 From the US Patent and Trademark Office Re.: U.S. Appl. No. 10/868,802.
Response Dated Jun. 16, 2009 to Official Action of Apr. 6, 2009 From the US Patent and Trademark Office Re.: U.S. Appl. No. 11/374,969.
Anderluh et al. "A Common Motif in Proparts of Cnidarian Toxins and Nematocyst Collagens and its Putative Role", Biochimica et Biophysica Acta, 1476: 372-376, 2000.
Böttger et al. "GFP Expression in *Hydra*: Lessons From the Particle Gun", Development of Gene Evolution, 212: 302-305, 2002.
Fernadez-Alonso et al. "DNA Vaccination by Immersion and Ultrasound to Trout Viral Heamorrhagic Septicaemia Virus", Vaccine, 19: 3067-3075, 2001.
Hidaka et al. "Effects of Calcium on the Mechanical Properties of the Capsule Wall of Isolated Nematocysts From *Calliactis polypus*", Comparisons in Biochemistry and Physiology, 107A(1): 31-36, 1994.
Holstein et al. "An Ultrahigh-Speed Analysis of Exocytosis: Nematocyst Discharge", Science, New Series, 223(4638): 830-833, 1984.
Kimball et al. "Efficacy of a Jellyfish Sting Inhibitor in Preventing Jellyfish Stings in Normal Volunteers", Wilderness and Environmental Medicine, 15: 102-108, 2004.
Koch et al. "Spinalin, a New Glycine- and Histidine-Rich Protein in Spines of *Hydra* Nematocysts", Journal of Cell Science, 111: 1545-1554, 1998.
Lotan et al. "Delivery of a Nematocyst Toxin", Nature, XP008041281, 375(6531): 456, Jun. 8, 1995.
Opalinska et al. "Nucleic-Acid Therapeutics: Basic Principles and Recent Applications", Nature Reviews: Drug Delivery, 1: 503-514, 2002.
Tardent "The Cnidarian Cnidocyte, A High-Tech Cellular Weaponry", BioEssays, XP00804143, 17(4): 351-362, 1995.
Tardent et al. "Morphology and Morphodynamics of the Stenotele Nematocyst of *Hydra attenuata* Pall (Hydrozoa, Cnidaria)", Cell Tissue Research, 224(2): 269-290, 1982.
Thorington et al. "Control of Cnida Discharge: I. Evidence for Two Classes of Chemoreceptor", Biological Bulletin, 174: 163-171, 1988.
Verma et al. "The Achilles Heel of Gene Therapy", Genes and Resistance to Diseases, p. 148, 2000.
Weber "Nematocysts (Stinging Capsules of Cnidaria) as Donnan-Potential-Dominated Osmotic Systems", European Journal of Biochemistry, 184(2): 465-476, 1989.
Official Action Dated Jan. 9, 2012 From the US Patent and Trademark Office Re. U.S. Appl. No. 12/955,990.
Official Action Dated Dec. 21, 2011 From the US Patent and Trademark Office Re. U.S. Appl. No. 13/166,877.
Communication Pursuant to Article 94(3) EPC Dated Feb. 2, 2010 From the European Patent Office Re.: Application No. 01976586.6.
Response Dated May 17, 2010 to Communication Pursuant to Article 94(3) EPC of Feb. 2, 2010 From the European Patent Office Re.: Application No. 01976586.6.
Official Action Dated Jun. 5, 2012 From the US Patent and Trademark Office Re. U.S. Appl. No. 12/588,368.
Notice of Allowance Dated Jun. 14, 2012 From the US Patent and Trademark Office Re. U.S. Appl. No. 13/166,877.
Notice of Allowance Dated Aug. 16, 2011 From the US Patent and Trademark Office Re.: U.S. Appl. No. 11/374,969.
Notice of Allowance Dated Aug. 22, 2012 From the US Patent and Trademark Office Re. U.S. Appl. No. 12/588,368.
Office Action Dated Sep. 2, 2010 From the Israeli Patent Office Re.: Application No. 155097 and its Translation Into English.
Official Action Dated Sep. 24, 2010 From the US Patent and Trademark Office Re.: U.S. Appl. No. 12/616,801.

(56) References Cited

OTHER PUBLICATIONS

Hyde "Skin, Hair, and Nails", The Nemours Foundation, Kidshealth, Retrieved From the Internet, p. 1-7, Apr. 21, 2001.
Official Action Dated Oct. 19, 2011 From the US Patent and Trademark Office Re. U.S. Appl. No. 13/166,877.
Official Action Dated Sep. 21, 2011 From the US Patent and Trademark Office Re. U.S. Appl. No. 12/955,990.
Response Dated Oct. 17, 2011 to Official Action of Sep. 21, 2011 From the US Patent and Trademark Office Re. U.S. Appl. No. 12/955,990.
Applicant-Initiated Interview Summary Dated Oct. 11, 2012 From the US Patent and Trademark Office Re. U.S. Appl. No. 12/955,990.
Applicant-Initiated Interview Summary Dated Oct. 18, 2012 From the US Patent and Trademark Office Re. U.S. Appl. No. 12/955,990.
Response Dated Nov. 21, 2011 to Official Action of Oct. 19, 2011 From the US Patent and Trademark Office Re. U.S. Appl. No. 13/166,877.
Communication Pursuant to Rules 70(2) and 70a(2) EPC Dated Nov. 26, 2012 From the European Patent Office Re. Application No. 06728266.5.
Summons to Attend Oral Proceedings Pursuant to Rule 115(1) EPC Dated Feb. 16, 2012 From the European Patent Office Re.: Application No. 01976586.6.
Official Action Dated Feb. 16, 2012 From the US Patent and Trademark Office Re. U.S. Appl. No. 12/588,368.
Office Action Dated Dec. 23, 2012 From the Israel Patent Office Re. Application No. 199236 and its Translation Into English.
Notice of Allowance Dated Mar. 24, 2011 From the US Patent and Trademark Office Re.: U.S. Appl. No. 12/616,801.
Response Dated May 15, 2011 to Office Action of Feb. 27, 2011 From the Israeli Patent Office Re.: Application No. 164191.
Office Action Dated May 7, 2010 From the US Patent and Trademark Office Re.: U.S. Appl. No. 11/374,969.
Communication Pursuant to Article 94(3) EPC Dated Jul. 25, 2013 From the European Patent Office Re. Application No. 06728266.5.
Office Action Dated Jul. 29, 2010 From the Israel Patent Office Re. Application No. 199236 and its Translation Into English.
Office Action Dated Jul. 29, 2010 From the Israeli Patent Office Re.: Application No. 164191 and its Translation Into English.
Office Action Dated Apr. 11, 2011 From the US Patent and Trademark Office Re.: U.S. Appl. No. 11/374,969.
Examination Report Dated Feb. 28, 2013 From the Government of India, Patent Office, Intellectual Property Building Re. Application No. 2408/CHENP/2007.
Official Action Dated Dec. 27, 2012 From the US Patent and Trademark Office Re. U.S. Appl. No. 12/955,990.
Response Dated Dec. 22, 2010 to Official Action of Sep. 24, 2010 From the US Patent and Trademark Office Re.: U.S. Appl. No. 12/616,801.
Response Dated Nov. 22, 2010 to Office Action of Jul. 29, 2010 From the Israel Patent Office Re. Application No. 199236.
Response Dated Nov. 22, 2010 to Office Action of Jul. 29, 2010 From the Israeli Patent Office Re.: Application No. 164191.
Response Dated Nov. 24, 2010 to Office Action of Sep. 2, 2010 From the Israeli Patent Office Re.: Application No. 155097.

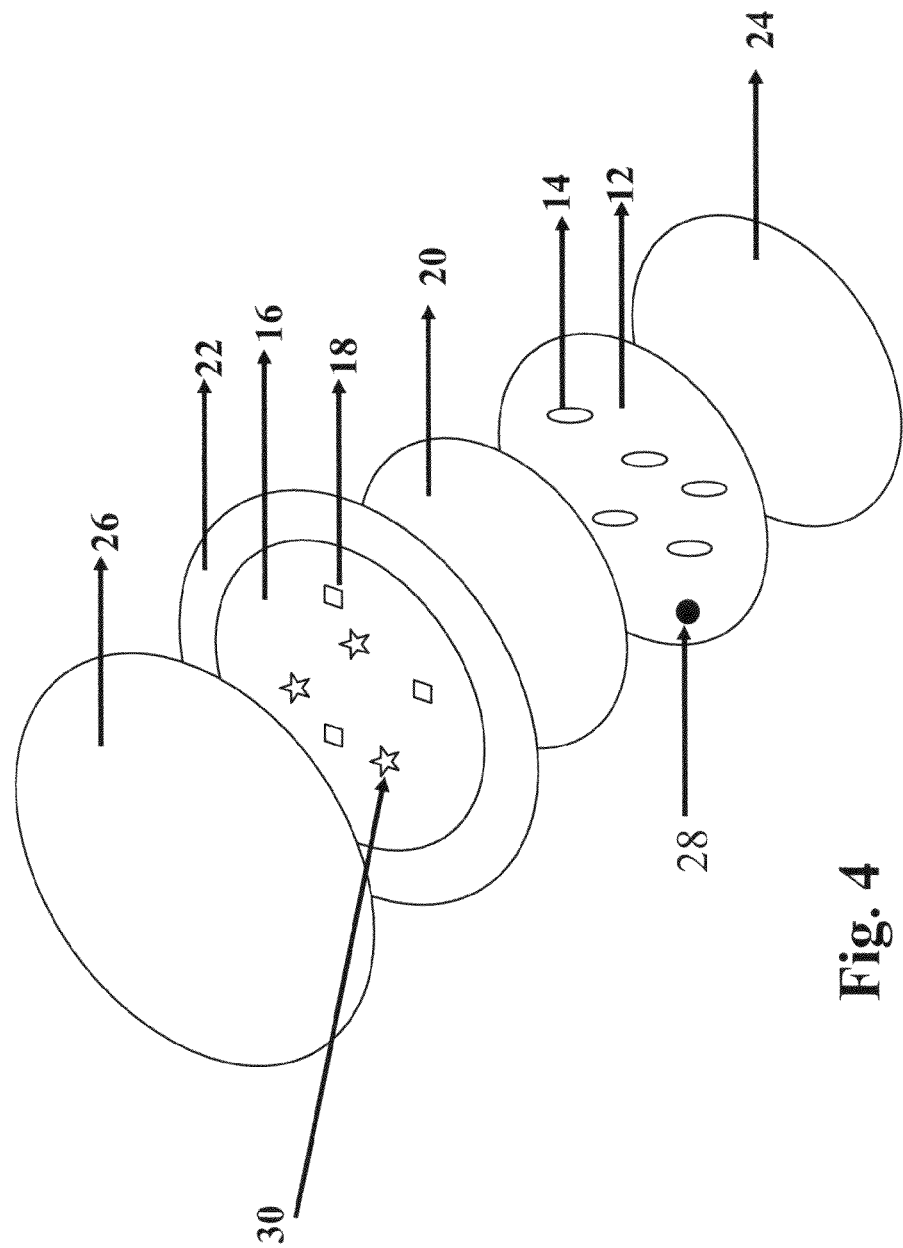

METHODS, COMPOSITIONS AND DEVICES UTILIZING STINGING CELLS/CAPSULES FOR CONDITIONING A TISSUE PRIOR TO DELIVERY OF AN ACTIVE AGENT

FIELD AND BACKGROUND OF THE INVENTION

The present invention relates to methods and devices utilizing stinging cells or capsules for conditioning a tissue prior to the delivery of an active agent. More particularly, the present invention relates to the use of stinging cells or capsules to enhance transdermal/dermal, transmembranal, transmucosal or transcuticular delivery.

Biological, biochemical and/or physical barriers often limit delivery of therapeutic agents to target tissue. For example, skin is a physical barrier, which must be traversed by a topically administered drug targeted at internal tissues.

To traverse the skin, drugs targeted at internal tissues (i.e., systemic administration) are often administered via transdermal drug delivery systems. Transdermal drug delivery may be targeted to a tissue directly beneath the skin or to capillaries for systemic distribution within the body by blood circulation.

Anatomically, the skin of a human body is subdivided into three compartments: an epidermis, a dermis and a subcutaneous layer. The outer layer of the epidermis, the stratum corneum, presents the greatest barrier to transdermal flux of drugs or other molecules into the body and of analytes out of the body. It is a complex structure of compact keratinized cell remnants (tough protein-based structures) separated by lipid domains. Compared to the oral or gastric mucosa, the stratum corneum is much less permeable to molecules either external or internal to the body. The stratum corneum has a thickness of only about ten to thirty microns and is formed from keratinocytes, which subsequently lose their nuclei and become corneocytes. This skin layer is continuously being renewed by shedding of corneum cells during desquamation and the formation of new corneum cells by the keratinization process. The epidermis, directly beneath the stratum corneum, also behaves as a lipid barrier whereas the dermis below that is permeable to many types of solutes.

Using a syringe and a needle or other mechanical devices, drugs may be injected into the subcutaneous space thus traversing the epidermis and dermis layers. Although the syringe and needle is an effective delivery device, it is sensitive to contamination, while use thereof is often accompanied by pain and/or bruising. In addition, the use of such a device is accompanied by risk of accidental needle injury to a health care provider. Mechanical injection devices based on compressed gasses have been developed to overcome the above-mentioned limitations of syringe and needle devices. Such devices typically utilize compressed gas (such as, helium or carbon dioxide) to deliver medications at high velocity through a narrow aperture.

Although such devices traverse some of the limitations mentioned above, their efficiency is medication dependent, and their use can lead to pain, bruising and lacerations.

Transdermal drug delivery usually excludes hypodermic injection, long-term needle placement for infusion pumps, and other needles which penetrate the skin's stratum corneum. Thus, transdermal drug delivery is generally regarded as minimally invasive.

Generally, transdermal drug delivery systems employ a medicated device or patch which is affixed to the skin of a patient. The patch allows a pharmaceutical agent contained within it to be absorbed through the skin layers and into the patient's blood stream. Transdermal drug delivery reduces the pain associated with drug injections and intravenous drug administration, as well as the risk of infection associated with these techniques. Transdermal drug delivery also avoids gastrointestinal metabolism of administered drugs, reduces the elimination of drugs by the liver, and provides a sustained release of the administered drug. This type of delivery also enhances patient compliance with a drug regimen because of the relative ease of administration and the sustained release of the drug.

However, many pharmaceutical agents are not suitable for administration via known transdermal drug delivery systems since they are absorbed with difficulty through the skin due to the molecular size of the pharmaceutical agent or to other bioadhesion properties of the agent. In these cases, when transdermal drug delivery is attempted, the drug may be found pooling on the outer surface of the skin and not permeating through the skin into the blood stream.

Generally, conventional transdermal drug delivery methods have been found suitable only for low molecular weight and/or lipophilic drugs such as nitroglycerin for alleviating angina, nicotine for smoking cessation regimens, and estradiol for estrogen replacement in post-menopausal women. Larger pharmaceutical agents such as insulin (a polypeptide for the treatment of diabetes), erythropoietin (used to treat severe anemia) and tinterferon (used to boost the immune systems cancer fighting ability) are all agents not normally effective when used with conventional transdermal drug delivery methods.

Methods of making hydrophilic drugs more disposed to transdermal delivery include incorporating within lipid vehicles (e.g., liposomes) or micelles or accompanying the delivery with skin permeation agents such that absorption of the active ingredient through the skin is enhanced. Such preparations can be directly applied to a skin region or delivered via transdermal devices such as membranes, pressure-sensitive adhesive matrices and skin patches. However, these passive transdermal drug delivery methods tend to be slow, and difficult to control.

Another method of transdermal drug delivery includes the use of a "gene gun," This device is capable of accelerating 20 to 70 μm diameter drug particles, or smaller DNA-coated gold particles, to supersonic velocities, such that the particles pass through the stratum corneum into the epidermis or dermis. A single particle, of that diameter, such as used in the gene gun, when fired at the stratum corneum at supersonic speeds, ruptures and tears through the tissues of the stratum corneum, epidermis and dermis, stopping and remaining at some depth which is determined by the initial velocity and mass of the particle. The resulting path through the above-mentioned tissues may be in the range of one to thirty μm depending on the tissue elasticity of the individual. Due to the elasticity of the skin, use of the gene gun does not form microconduits in the skin because the tissue is only temporarily pushed aside as the particle is forced through the skin.

One disadvantage associated with this method is that the rate of transport of molecules tends to diminish rapidly with increasing molecular size.

Other examples of transdermal drug delivery methods presently being investigated include the use of ultrasound (sonophoresis) to cause cavitations in the stratum corneum; laser ablation of a small region of the stratum corneum, thereby providing access to the epidermis; the use of electrical methods, including low voltage iontophoresis, wherein transport is believed to occur through pre-existing aqueous pathways; and the use of high voltage pulses to cause electroporation of the skin.

Other methods are based on arrays of micro-needles. The needles make micro size holes through the top layers of the skin, to deliver a wide variety of actives or drugs directly to the body. Examples of branded micro-needles include: Drug Mat (ThecaJect), Macroflux (alza), Microstructured transdermal system (3M), microTrans (Biovalue), Micro syringe catheter (EndoBionics), Micro pyramid (nanoPass), Simple choice (SpectRx), VaxMat (ThecaJect). The Micro-needles are made of various polymers such as silicon or metal-like titanium. The micro-needles can be drug-coated or hollow for drug delivery with or without energy assistance.

There are, however, disadvantages associated with each of these methods including pain and discomfort, skin irritation, the high cost and the large size of equipment required, and the potential for breaking of needles, which might remain embedded in the skin. Even with these recent developments, the low rate of transport of therapeutic molecules through the stratum corneum remains a common clinical problem.

To enhance transdermal drug delivery, there are known methods for increasing the permeability of the skin to drugs. For example, U.S. Pat. No. 5,885,211 is directed to thermal microporation techniques and devices to form one or more micropores in a biological membrane and methods for selectively enhancing outward flux of analytes from the body or the delivery of drugs into the body. PCT WO 00/03758 is directed to methods and apparatus for forming artificial openings in a selected area of a biological membrane using a pyrotechnic element that is triggered to explode in a controlled fashion so that the micro-explosion produces the artificial opening in the biological membrane to a desired depth and diameter. PCT WO98/29134 discloses a method of enhancing the permeability of a biological membrane, such as the skin of an animal, using microporation and an enhancer such as a sonic, electromagnetic, mechanical, thermal energy or chemical enhancer. Methods and apparati for delivery or monitoring using microporation also are described in PCT WO 99/44637, U.S. Pat. No. 6,022,316, PCT WO 99/44508, PCT WO 99/44507, PCT WO 99/44638, PCT WO 00/04832, PCT WO 00/04821, and PCT WO 00/15102. Generally, these methods are used in conjunction with traditional transdermal patches or membranes which rely on the diffusion of the agents through the skin.

Although transdermal delivery offers an alternative to some invasive delivery methods, the efficiency thereof is affected by the physical and chemical properties of the targeted therapeutic, diagnostic or cosmetic agent and physiological or pathological parameters such as the skin hydration, temperature, location, injury, and the body metabolism. There thus remains a need for improved methods and devices for transdermal delivery of these agents including methods of preconditioning skin tissue.

"Stinging cells" (e.g. cnidocytes, nematocytes and the like) or "stinging capsules" (e.g., cnidocysts, nematocysts and polar capsules) isolated therefrom have been proposed as suitable agents for tissue delivery of a therapeutic or cosmetic agents [U.S. Pat. App. No. 20040224013 and U.S. Pat. No. 6,613,344]. Cnidaria (hydras, sea anemones, jellyfish and corals) are aquatic animals, which possess a variety of compounds which are stored and delivered via specialized capsules (cnidocysts), which form a part of specialized cells termed stinging cells (cnidocytes, nematocytes, ptychocytes and the like). The stinging capsules are hard and dense and filled with liquid containing a highly folded, inverted tubule which may also feature specialized structures such as shafts, barbs, spines, and/or stylets. In nature, the cnidocyst discharges and releases its tubule into tissue following physical or chemical triggering.

Discharge is initiated by a rapid osmotic influx of water which generates an internal hydrostatic (liquid) pressure of 150 atmospheres forcing capsule rupture and ejection of the tubule [Holstein, T., and Tardent, P. (1984) *Science*, 223(4638), 830-3]. During ejection, the long coiled and twisted tubule is averted and its length increases by 95%. Accelerating at 40,000 g, the tubule untwists to generate a torque force, which rotates the tubule several times around its axis. These mechanical processes generate a powerful driving force, which enables efficient delivery of the compounds, the toxins and enzymes stored within the capsule [Lotan et al., 1995 *Nature*, 375(6531), 456: Lotan et al., 1996 *J Exp Zool*, 275(6), 444-51; Tardent 1995, *BioEssays*, 17(4), 351-362]. This process, which occurs within microseconds, is among the most rapid exocytosis events in biology [Holstein, T., and Tardent, P. (1984) *Science*, 223(4638), 830-3].

The Cnidaria family which encompasses 10,000 known species includes sedentary single or colonial polyps and pelagic jellyfish. In some of these species, cnidocytes account for more than 45% of the cells present [Tardent 1995, *BioEssays*, 17(4), 351-362].

There are at least three dozen known types of cnidocysts (also termed cnidae) including more than 30 varieties of nematocysts found in most Cnidaria and spirocysts, and ptychocysts found mainly in the Cnidaria class Anthozoa [Mariscal 1974, *Coelenterate biology: reviews and new perspectives*, Academic Press, New York.].

As is further detailed herein, the present invention utilizes stinging cells such as cnidocytes, or stinging capsules (cnidocysts) isolated therefrom for preconditioning the skin and aiding the subsequent dermal or transdermal delivery of agents into the skin while being devoid of the limitations inherent to prior art invasive or non-invasive delivery devices and compositions.

SUMMARY OF THE INVENTION

It is an object of the present invention to provide methods for preconditioning a tissue prior to delivery of an active agent into and/or through the tissue.

It is another object of the present invention to provide methods for delivery of an active agent into and/or through a tissue.

It is another object of the present invention to provide methods and pharmaceutical compositions for orientating stinging capsules/cells with respect to a tissue.

It is yet another object of the present invention to provide a device for delivery of an active agent through a tissue.

Hence, according to one aspect of the present invention there is provided a method of preconditioning a tissue prior to delivery of an active agent into and/or through the tissue, the method comprising: (a) administering onto the tissue at least one stinging capsule/cell; and (b) discharging the at least one stinging capsules/cells to thereby deliver a tubule of the at least one stinging capsule/cell onto the tissue thus preconditioning the tissue for subsequent delivery of the active agent into and/or through the tissue.

According to another aspect of the present invention there is provided a method of delivery of an active agent into and/or through a tissue, the method comprising: (a) preconditioning the tissue by: (i) administering onto the tissue at least one stinging capsule/cell; and (ii) discharging the at least one stinging capsule/cell to thereby deliver a tubule of the at least one stinging capsule/cell onto the tissue thus preconditioning the tissue for subsequent delivery of the active agent into and/or through the tissue; and subsequently (b) administering the active agent onto the tissue, thereby effecting the delivery of the active agent into and/or through the tissue.

According to still another aspect of the present invention there is provided a pharmaceutical composition comprising at least one stinging capsule/cell and an orientation and proximity agent selected for: (i) positioning the at least one stinging capsule/cell in intimate proximity with a tissue; and (ii) orientating the at least one stinging capsule/cell such that the opening tip of the stinging capsule substantially faces the tissue.

According to an additional aspect of the present invention there is provided a method of orientating stinging capsules/cells with respect to a tissue, the method comprising contacting at least one stinging capsule/cell, an orientation and proximity agent and the tissue, wherein the orientation and proximity agent is selected for: (i) positioning the at least one stinging capsule/cell in intimate proximity with a tissue; and (ii) orientating the at least one stinging capsule/cell such that the opening tip of the stinging capsule substantially faces the tissue.

According to further features in preferred embodiments of the invention described below, the delivery of an active agent is dermal, interdermal and/or transdermal delivery.

According to still further features in the described preferred embodiments the delivery of an active agent is transmucosal.

According to still further features in the described preferred embodiments the delivery of an active agent is transmembranal.

According to still further features in the described preferred embodiments the delivery of an active agent is transcuticular.

According to still further features in the described preferred embodiments the tissue is selected from the group consisting of skin tissue, mucous tissue, membranal tissue and cuticular tissue.

According to further features in preferred embodiments of the invention described below, the at least one stinging capsule/cell is of an organism having an endogenous toxin naturally stored within its stinging cell which is substantially non-toxic to mammals.

According to still further features in the described preferred embodiments the endogenous toxin is non-functional.

According to still further features in the described preferred embodiments the at least one stinging capsule/cell is from an organism of a class selected from the group consisting of Anthozoa, Hydrozoa, Hexacorallia, and Scyphozoa.

According to still further features in the described preferred embodiments the at least one stinging capsule/cell is from an organism of a phylum selected from the group consisting of Cnidaria, Dinoflagellata and Myxozoa.

According to still further features in the described preferred embodiments, the at least one stinging capsule/cell is from a species selected from the group consisting of Rhopilema nomadica, Hydra vulgaris, Hydra hymanae, Metridium, Nematostella vectensis, Rhodactis rhodostoma, Heliofungia actiniformis and Aiptasia diaphana.

According to still further features in the described preferred embodiments, the stinging capsule form a part of the stinging cell.

According to still further features in the described preferred embodiments, the stinging cell forms a part of a tentacle, a filament or an acontia.

According to still further features in the described preferred embodiments, the discharging is effected by hydration, a change in pH, addition of a biochemical or addition of a chemical.

According to still further features in the described preferred embodiments the at least one stinging capsule/cell is provided in a composition which further comprises an orientation and proximity agent selected for: (i) positioning the at least one stinging capsule/cell in intimate proximity with the tissue; and (ii) orientating the at least one stinging capsule/cell such that the opening tip of the stinging capsule substantially faces the tissue.

According to still further features in the described preferred embodiments, the orientation and proximity agent is selected from the group consisting of a negatively charged agent, an adhesive agent and an amphoteric agent.

According to still further features in the described preferred embodiments, the orientation and proximity agent is selected from the group consisting of an anionic polymer, polyacrylic acid (PAA), a poly saccharine, alginic Acid, Na alginate, gelatin, hydroxy propyl methyl cellulose, carboxy methyl cellulose, gum karaya, gum tragacanth, poly ethylene oxide, poly vinyl alcohol, starch, starch, carbomer, lectin, invasion and bacterial fimbrin.

According to still further features in the described preferred embodiments the stinging tubules are less than one μm in diameter.

According to still further features in the described preferred embodiments the at least one stinging capsule/cell is formulated in a topical composition selected from the group consisting of a gel, a cream, an ointment, a paste, a lotion, a milk, a suspension, an aerosol, a spray, a foam and a serum.

According to still further features in the described preferred embodiments the at least one stinging capsule/cell is administered onto the tissue using an applicator.

According to still further features in the described preferred embodiments the applicator is selected from the group consisting of a patch, a foil, a plaster, polymer and a pad.

According to still further features in the described preferred embodiments the active agent is selected from the group consisting of a therapeutic agent, a cosmetic agent and a diagnostic agent.

According to still further features in the described preferred embodiments the therapeutic agent is selected from the group consisting of a drug, a nucleic acid construct, a vaccine, a hormone, an enzyme and an antibody.

According to still further features in the described preferred embodiments the cosmetic agent is selected from the group consisting of a cosmetic dye, an anti wrinkling agent, an anti-acne agent, a vitamin, a skin peel agent, a hair follicle stimulating agent and a hair follicle suppressing agent.

According to still further features in the described preferred embodiments, the diagnostic agent is an antibody, a chemical or a dye.

According to still further features in the described preferred embodiments, the stinging capsules/cells are preloaded with an active substance or are in a composition which comprises the active substance.

According to still further features in the described preferred embodiments the active agent and the active substance are identical.

According to still further features in the described preferred embodiments the active agent and the active substance are non-identical.

According to yet an additional aspect of the present invention there is provided a device for delivery of an active agent through a tissue, the device comprising: (i) a first compartment comprising at least one stinging cell/capsule; (ii) a second compartment comprising an active agent.

According to yet an additional aspect of the present invention, the first and said second compartments are arranged as partitioned layers in the device.

According to yet an additional aspect of the present invention, the device further comprises a void color indicator.

According to yet an additional aspect of the present invention, the delivery is immediate delivery or delayed delivery.

The present invention successfully addresses the shortcomings of the presently known configurations by compositions, devices and methods using same for preconditioning a tissue prior to subsequent delivery of an active agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The application file contains at least one drawing executed in color. Copies of this patent or patent application with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the drawings:

FIG. 1a shows the bright field of two capsules labeled with rhodamine ionic micelles. The arrows point to the tip of the capsule from where the tubule is released. FIG. 1b shows the same capsules under UV light. The red rhodamine fluoresce stains the tip of the capsule from where the tubule is released (indicated by arrows).

FIG. 4 is a schematic illustration of a configuration of a stinging capsule patch for immediate and control delay drug release generated according to the teachings of the present invention.

DESCRIPTION OF THE PREFERRED EMBODIMENTS

Figure 1:
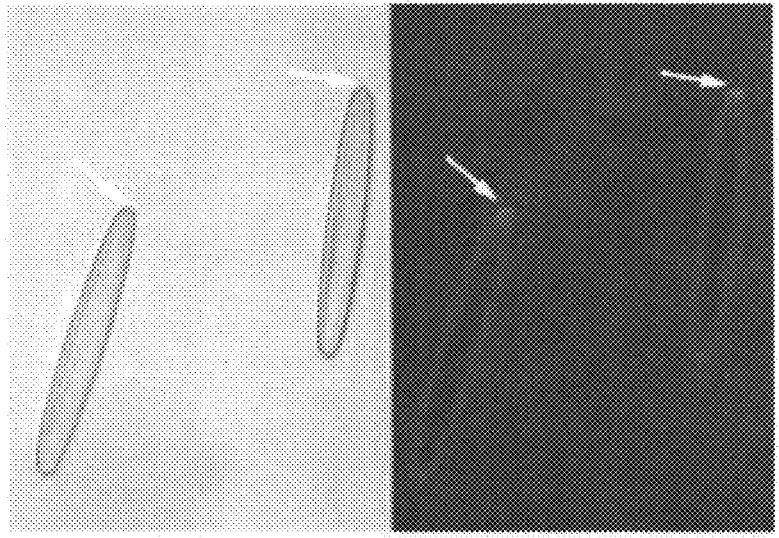
FIGS. 1a-b are images captured by microscopy depicting the asymmetric nature of the stinging capsules.

The present invention relates to compositions, devices and methods of using same for enhancing delivery of active agents through a tissue such as skin. Preconditioning the skin with stinging cells/capsules augments the diffusion of a subsequent active agent through the skin.

The principles and operation of enhanced delivery of an active agent through a tissue and preconditioning of that tissue may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For several years, transdermal drug delivery systems have been employed to effectively introduce a limited number of drugs through unbroken skin. Aside from comfort and convenience, transdermal systems avoid the barriers, delivery rate control problems and potential toxicity concerns associated with traditional administration techniques, such as oral, intramuscular or intravenous delivery. Although transdermal delivery offers an alternative to some invasive delivery methods, the efficiency thereof is affected by the physical and chemical properties of a drug and physiological or pathological parameters such as the skin hydration, temperature, location, injury, and the body metabolism.

Methods of enhancing transdermal delivery include the use of microneedles, ultrasound or thermal microporation. There are, however, disadvantages associated with each of these methods including pain and discomfort, skin irritation, the high cost and the large size of equipment required, and the potential for breaking -of needles, which might remain embedded in the skin. Even with these recent developments, the low rate of transport of therapeutic molecules through the stratum corneum remains a common clinical problem.

The use of stinging capsules/cells from Cnidaria as an efficient and pain-free means of delivering active agents through the skin is described in U.S. Pat. App. No. 20040224013 and U.S. Pat. No. 6,613,344 to the present inventors.

While reducing the present invention to practice, the present inventors have uncovered that stinging capsule tubules which remain embedded within skin tissue following discharge can be used for subsequent transdermal delivery of active agents.

Thus, according to one aspect of the present invention there is provided a method of preconditioning a tissue prior to delivery of an active agent into and/or through the tissue.

The method of this aspect of the present invention is effected by (a) administering onto the tissue at least one stinging capsule/cell; and (b) discharging at least one stinging capsule/cell to thereby deliver a tubule of at least one stinging capsule/cell onto the tissue thus preconditioning the tissue for subsequent delivery of the active agent into and/or through the tissue.

As used herein, the term "tissue" refers to an external body tissue, including skin tissue, membrane tissue (e.g. eye), mucous tissue (e.g., the mucosal barrier of the mouth, the throat and the external female genitalia) and cuticular tissue.

As used herein the phrase "preconditioning a tissue" refers to preparing the tissue in such a manner as to be more amenable to the diffusion through it of active agents. In the present invention, this is effected by tubules which remain in the tissue following stinging capsule/cell discharge. The tubules serve as open channels for subsequent delivery of active agents.

As used herein, the term "active agent" refers to a therapeutic, diagnostic or cosmetic agent.

As used herein, the phrase "dermal delivery of an active agent" refers to topical application of the active agent to the outer layer of the epidermis, i.e. the stratum corneum.

As used herein, the phrase "interdermal delivery of an active agent" refers to the delivery of the active agent such that it penetrates the top layer of the epidermis to localize mainly in the epidermis and the dermis skin layers.

As used herein the phrase "transdermal delivery of an active agent" refers to delivery of an agent to a tissue directly beneath the inner layer of the skin, i.e. in the subcutaneous space or to capillaries for systemic distribution within the body by blood circulation.

As used herein, the phrase "stinging cells" refers to the specialized cells (e.g. cnidocytes or nematocytes) present in, for example, all members of the phylum Cnidaria, Myxozoa, and Dinoflagellata. A stinging cell contains the "stinging capsule".

As used herein the phrase "stinging capsules" refers to the capsules (cnidocysts), which house the delivery tubule. The stinging capsules act as microscopic syringes and serve as a prey or defense mechanism. The stinging capsule is a hardened dense capsule filled with liquid, containing a highly folded inverted tubule which sometimes features specialized structures such as shafts, barbs, spines, and/or stylets.

The stinging capsule according to the teachings of the present invention can be an isolated stinging capsule or alternatively it can form a part of a stinging cell. In any case, the stinging capsule or cell is derived from an organism of the phylum Cnidaria, Myxozoa, or Dinoflagellata.

The stinging cell or capsule utilized by the present invention is preferably derived from an organism of the class Anthozoa, Hydrozoa or Scyphozoa. More specifically, the stinging cell/capsule utilized by the present invention can be derived from, for example, subclasses Hexacorallia or Octocorallia of the class Anthozoa, (mostly sea anemone and corals), subclasses Siponophora or Hydroida of the class Hydrozoa, or from subclasses Rhisostomeae or Semastomeae of the class Scyphozoa.

Stinging capsules from such organisms include toxins, which are non-toxic to humans, and other mammals. As such, these stinging cells or capsules isolated therefrom are ideally suited for safe and efficient delivery of a therapeutic or cosmetic agent into mammalian tissue.

It will be appreciated that the use of stinging cells from organisms which sequester toxins that are not fatal but cause only minor irritations to, for example, mammals, is also envisioned by the present invention.

In addition, stinging cells from other sources can also be utilized by the present invention provided inactivation of the endogenous toxin is effected prior to use.

Such inactivation can be effected via one of several methods, including but not limited to, temperature or chemical denaturation, enzymatic inactivation or ligand inactivation (e.g., Fab fragment of an antibody).

As is demonstrated in U.S. Pat. No. 6,613,344, toxins endogenous to cnidocysts can be efficiently and easily inactivated by incubating isolated cnidocysts at 45° C. for several hours. Alternatively, incubation at a high temperature of 70-95° C. for several minutes can also be utilized by the present invention.

As demonstrated in U.S. Pat. No. 6,613,344, incubation of cnidocysts at 45° C. for 22 hours does not damage or trigger activation of the cnidocyst. Such conditions are effective in denaturing polypeptides stored within the cnidocyst, such as the polypeptide toxins and enzymes delivered by the tubule of the cnidocyst. It will be appreciated that since organisms of, for example, the phylum Cnidaria habitat aquatic environments, which are characterized by temperatures well below 30° C., polypeptides stored within their stinging capsules can be denatured via incubation in temperatures well above 30° C.

The stinging cell or the stinging capsule of the present invention can be isolated from a cell extract prepared from organs or parts of an organism, which contain the stinging cells (for example a whole hydra, tentacles or filaments). Alternatively, stem cells, which give rise to cnidocytes or cnidocysts, can be isolated and cultured or utilized directly.

The main differences between the stinging cells are in their capsule shape and size and in their tubule dimensions. Examples of species containing different tubules include but are not limited to Rhopilema nomadica (400 μm hollow tubule length with tiny hollow barbs), Hydra vulgaris, Hydra hymanae, Metridium senile (200 μm tubule length), Nematostella vectensis (200 μm tubule length), Rhodactis rhodostoma (9 mm tubule length), Heliofungia actiniformis (1000 μm tubule length) and Aiptasia diaphana (150 μm tubule length, in which only the 50-60 μm tip penetrates the skin). Selection of the stinging cell/capsule is dependent upon target organ thereof. For example, if the active agent is used to treat the skin, typically a short tubule is used. For systemic or subcutaneous administration, longer tubule lengths may be used. Selection of the stinging cell-capsule is also dependent upon the administered agent. If the administered agent diffuses easily through the skin due to its physiochemical properties, a short tubule may be used. Conversely, if the administered agent does not diffuse easily through the skin a longer tubule may be used to aid in its administration.

It will be appreciated that tubules which are less than one μm in diameter may be preferably used in accordance with this aspect of the present invention to prevent pain and minimize damage to the skin.

It will be appreciated that organs, tentacles, or parts of an organism, and the whole organism (hydra for example), which contain the stinging cells can be used without the need for prior isolation of individual stinging cells or for isolation of the capsules from the cells.

As mentioned, the at least one stinging capsule/cell of the present invention may be administered onto the outer surface of the skin. Methods, formulations and devices for administering the stinging capsules/cells of the present invention are further described hereinbelow.

As used herein the term "discharging" refers to the activation of at least one stinging capsule/cell whereby the tubule contained within is released and penetrates the tissue. This may be triggered by hydration, a change in pH, a biochemical (e.g. an enzyme) or a chemical.

Chemical triggering can be mediated by substances such as free and conjugated N-acetylated sugars or low molecular weight amino compounds which are known to be detected by at least two classes of stinging cell chemoreceptors. Sodium thiocyanate (NaSCN) is capable of triggering discharge of cnidocysts. In addition, Lubbock and Amos [*Nature*, 290 (5806), 500-1, 1981] have shown that isolated cnida (cnidocysts) can discharge normally when placed in buffered EGTA or 10 mM citrate solution; Weber [*Eur J Biochem*, 184(2), 465-76 (1989)] demonstrated the effect of dithioerthritol or proteases on discharging isolated cnida and Hidaka

[*Advances in Comparative and Environmental Physiology*, 15, 45-76 (1993)] discussed various agents which can trigger cnida discharge.

Alternatively, discharge may be effected by hydration with a water-based composition such as saline or water, thereby opening channels in the tissue and enhancing delivery of a subsequent topically applied agent.

Preferably, the stinging capsules are provided in a composition which further comprises an orientation and proximity agent selected for positioning at least one stinging capsule/cell in intimate proximity with the skin; and orientating the at least one stinging capsule/cell such that the opening tip of the stinging capsule from where the tubule discharges substantially faces the skin.

As used herein, the phrase "opening tip" refers to a part of the stinging cell from where the tubule discharges. The opening tip includes the operculum.

As used herein, the phrase "in intimate proximity with the tissue" refers to a range of distances from touching the tissue to the furthest distance from the tissue that the tubules are still able to penetrate.

As described in Example 1 of the Examples section which follows, the stinging capsules have asymmetric characteristics, such that the opening tip is positively charged and the opposite end is not. Thus, by using specific agents capable of binding to the opening tip on one hand and a tissue on the other, the capsules can be orientated so that a high proportion of stinging cells come into physical contact with a tissue, thereby enhancing subsequent delivery of an active agent. Specifically, the opening tip is orientated, such that it substantially faces the tissue. The term "substantially facing the tissue" as used herein describes any angle of the opening tip which will allow penetration of the tubule into the tissue. Preferably, the opening tip may be perpendicular to the tissue surface (at an angle of 90°) allowing for the greatest surface area of the opening tip to be in touch with the tissue's surface. However, the opening tip may also be orientated at other angles to the tissue.

A number of substances may be used as the orientation and proximity agent of the present invention. For example, the orientation and proximity agent may be a negatively charged polymer (such as at least partially negatively charged polymer), which interacts with the positively charged opening tip, an adhesive (e.g., bioadhesive) or an amphoteric substance. Examples of orientation and proximity agents which may be used in accordance with the present invention include, but are not limited to synthetic anionic polymers such as polyacrylic acid (PAA), poly saccharines, such as alginic Acid, Na alginate, hydroxy propyl methyl cellulose, carboxy methyl cellulose, and others poly saccharines such as gum karaya, gum tragacanth, poly ethylene oxide, poly vinyl alcohol, starch, lecithin. As mentioned, the orientation and proximity agent can be amphoteric for example gelatin, caseine and lecitin. Examples of adhesives or bioadhesives include, but are not limited to, carbomer, lectin, bacterial fimbrins and invasins.

The capsules can be pretreated with the orientation and proximity agents. Alternatively, the orientation and proximity agents can be introduced into the composition in which the capsules are formulated.

The stinging cells/capsules of the present invention may be applied topically onto a tissue e.g. in a gel. In this way, the number of tubules need not be limited to one particular area of the tissue as is the case with a chip or an array, but may be spread over larger areas. This may be particularly useful when applying active agents to treat the skin, for example in treating skin conditions such as acne or psoriasis.

Alternatively, as described herein below, for more accurate dosing of an active agent, the stinging capsules can be applied onto a tissue using an applicator such as a patch (as further described hereinbelow), a foil, a plaster, a polymer or a pad which can be prepared with an exact quantity of stinging capsules.

To stabilize the stinging cells/capsules and to possibly enhance triggering efficiency, the stinging cells/capsules of the present invention are preferably included in a pharmaceutical composition. Such pharmaceutical compositions comprise a carrier. The carrier generally should not affect the ability of the stinging cells to discharge following triggering, although in some instances, a carrier which inhibits triggering mediated by hydration can also be utilized by the present invention as described herein below. The pharmaceutical composition of the present invention is formulated for topical, transdermal, dermal, transmucosal or transnasal applications. For topical application, the stinging cells/capsules may be suspended in a gel suitable for topical applications. Other examples of pharmaceutical compositions suitable for topical, transmucosal or transnasal applications include, but are not limited to creams, ointments, pastes, lotions, milks, suspensions, foams and serum.

For transdermal, dermal, interdermal, transmucosal or transnasal administration, the stinging cells can be conveniently delivered in the form of a liquid or an aerosol spray presentation form, a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount.

When the stinging capsules/cells are activated by a hydrating agent, the stinging capsules/cells are typically formulated in a dry composition e.g. a powder or an anhydrous formulation, for example an ethanol based solid gel. Alternatively, the stinging capsules/cells are formulated in a hydrated formulation as described above. If a hydrated formulation is preferred, the pharmaceutical composition of the present invention typically includes an agent which inhibits discharge of the stinging cells/capsules. In such cases, the pharmaceutical composition also includes a chemical activator, such as, for example NaSCN or EGTA, which can be applied prior to, or following, application of the pharmaceutical composition and which triggers discharge of the stinging cells.

As mentioned, a variety of active agents (e.g., therapeutic agents, cosmetic agents and diagnostic agents) can be administered following discharge of the stinging capsules of the present invention.

A therapeutic agent can be any biological active factor such as, for example, a drug, a nucleic acid construct, a vaccine, a hormone, an enzyme, small molecules such as for example iodine or an antibody. Examples of therapeutic agents include, but are not limited to, antibiotic agents, free radical generating agents, anti fungal agents, anti-viral agents, non-nucleoside reverse transcriptase inhibitors, protease inhibitors, non-steroidal anti inflammatory drugs, immunosuppressants, anti-histamine agents, retinoid agents, tar agents, antipuritic agents, hormones, psoralen, and scabicide agents. Nucleic acid constructs deliverable by the present invention can encode polypeptides (such as enzymes ligands or peptide drugs), antisense RNA, or ribozymes.

A cosmetic agent of the present invention can be, for example, an anti-wrinkling agent, an anti-acne agent, a vitamin, a skin peel agent, a hair follicle stimulating agent or a hair follicle suppressing agent. Examples of cosmetic agents include, but are not limited to, retinoic acid and its derivatives, salicylic acid and derivatives thereof, sulfur-containing D and L amino acids and their derivatives and salts, particularly the N-acetyl derivatives, alpha-hydroxy acids, e.g., glycolic acid, and lactic acid, phytic acid, lipoic acid and many other agents which are known in the art.

In addition, the stinging cells or isolated capsules of the present invention can be used to produce permanent or temporary tattoos. For such purposes, a predetermined pattern of stinging cells/capsules can be attached to a support such as a plaster, foil or the like. The stinging cells/capsules can be activated and the cosmetic dye can subsequently be applied. The dye would then diffuse into the skin through the open tubules to form a predetermined dye pattern (tattoo). By using the composition of the present invention, the tattoo can be altered (e.g. the color) by the subsequent addition of different colored dyes, each diffusing through the activated tubules, as long as the tubules remain fixed in the skin and the predetermined dye pattern is unaltered.

A diagnostic agent of the present invention may be an antibody, a chemical or a dye specific for a molecule indicative of a disease state.

It will be appreciated that the stinging capsules/cells of the present invention can be preloaded with a substance (e.g., therapeutic substance, cosmetic substance or diagnostic substance) which may be identical to, or different from the agent administered following discharging and preconditioning. For example, the preloaded therapeutic substance can be a prodrug, which after tubule discharge and penetration into a tissue, is converted into an active form whilst in the tissue via the subsequent addition of a chemical activator (i.e., agent).

Other examples of substances of the present invention which may be preloaded into the stinging capsules/cells can be any of the foregoing agents described hereinabove.

The active agent may be disposed within the liquid stored in the stinging cell or the stinging capsule. In such a case, the stinging cell or the isolated capsule is loaded with the active agent via any one of several methods generally known in the art such as, but not limited to, diffusion, electroporation, liposome fusion, microinjection and the like.

Alternatively, the active agent may be disposed in a liquid surrounding the stinging cell or the isolated capsule. In such a case, the stinging capsule's natural mechanism of osmotically collecting liquid from the environment following triggering (further detailed hereinabove) pumps the substance into the stinging cell just prior to or during the discharge.

In any case, since the stinging capsule is highly permeable to water and molecules, loading of substances of the present invention prior to or following discharge can be easily achieved.

According to the teachings of the present invention, the stinging cells/capsules described above can also be utilized in a delivery device useful for the immediate or delayed delivery of an active agent through a tissue.

As used herein, the phrase "immediate delivery of an active agent" refers to the delivery of an active agent concomitant with the discharge of the stinging tubule.

As used herein, the phrase "delayed delivery of an active agent" refers to the delivery of any active agent which has not been delivered via the discharge of the stinging tubule.

Thus, according to yet another aspect of the present invention there is provided a delivery device comprising a first compartment comprising at least one stinging cell/capsule and a second compartment comprising the active agent.

In one embodiment of this aspect of the present invention, the above-described compartments of the delivery device are arranged as partitioned layers.

Such a configuration of the device is specifically shown in FIG. 4 and is referred to herein as device 10.

Device 10 includes a stinging layer 12 comprising at least one stinging cell/capsule 14, an active layer 16 comprising an active agent 18 and a separator 20 interposed between stinging layer 12 and active layer 16.

Upon disintegration of separator layer 20, by a mechanical force, e.g. pressure, stinging cells/capsules 14 discharge and deliver (via their tubules) active agent 18 into the tissue (as described hereinabove).

The margins of active layer 16 preferably comprise an adhesive skin margin 22 for steady contact with the tissue similar to the adhesive layer in a household plaster. The at least one stinging cell/capsule 14 is preferably formulated in a dry composition (e.g. a powder or an anhydrous formulation, for example an ethanol based solid gel), which may further comprise an orientation and proximity agent (as described hereinabove). Active agent 18 is preferably formulated as a thin watery gel or in a water-based solution in an amount which is sufficient to hydrate stinging cells/capsules 14 and is spread as a uniform layer.

Device 10 further includes a protective layer 24 disposed external to stinging layer 12 and/or a second protective layer 26 disposed external to active layer 16. Protective layer 24, which is in direct contact with the at least one stinging cell/capsule 14, is removed prior to patch application on the tissue. Protective layer 26 is in direct contact with active agent 18 and serves as a support maintaining active agent 18 in the vicinity of the patch.

Protective layer 26 can be, for example, a patch, a foil, a film, a plaster, a polymer or a pad or any material capable of supporting active agent 18 in a manner suitable for application to, for example, a skin region of the individual.

Device 10 further includes a void color indicator 28 in stinging layer 12 that displays a particular color indicating activation of stinging cells/capsules 14. This may serve for monitoring product shelf-live and proper storage conditions. Alternatively, void color indicator 28 may be present in active layer 16 where it could be used to assure process termination after application on the tissue and once delivery is complete.

Device 10 can be removed immediately following delivery of active agent 18 as described herein above. Alternatively, device 10 may remain fixed on the tissue and used for a controlled delay release of the any active 18 that has not already been administered through immediate delivery. In addition, active substance 30, which may or may not be identical with active agent 18, may be present in active layer 16 or applied following the immediate and delayed release of active agent 18, such as after removal of protective layer 26. Active substance 30 then diffuses through the open tubules through the tissue.

As mentioned hereinabove, the present invention can be utilized to deliver a variety of active therapeutic agents. Such therapeutic agents combined with the effective delivery of the present invention can be utilized to topically or systemically treat a variety of disorders, which are not necessarily confined to the treated tissue (e.g., skin). As shown in Example 2 of the Examples section which follows, using the teachings of the present invention, the present inventors were able to reduce blood glucose levels in nude mice.

The stinging cells/capsules of the present invention can also be utilized for vaccination. Vaccine antigens can be delivered to specialized immune cells underlying the skin or into blood circulation (as described above).

Absorption into the blood stream following transdermal delivery will most likely result in transport of the antigen to the phagocytic cells of the liver, spleen, and bone marrow.

Since such cells serve as antigen presenting cells, a strong immunogenic response will be elicited leading to effective immunization.

Thus, the present invention overcomes the limitations of prior art devices and methods while providing a safe, efficient and contamination risk free method for delivering agents across epidermal, mucosal or membranal barriers.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Orientation of the Capsules

In order to orientate the capsules of the present invention, it was important to ascertain whether the capsules have asymmetric characteristics.

Methods

Specimen Preparation—Capsules from aiptasia diaphana were isolated by Na citrate followed by percoll gradient and observed on microscopic slides.

Fluorescent ionic micelle preparation—Rhodamine ionic micelles were prepared from SDS, cyclometicone and rhodamine.

Staining/labeling protocol—The capsules were exposed to ionic micelles containing rhodamine for 10 minutes. Capsules were washed three times to remove the excess of micelles.

The capsules were also exposed to the ionic fluorescent dye fluoreceine (Sigma, Aldrich) at a concentration of 0.1% for 15 minutes. The capsules were washed three times so that most of the free dye was removed.

Analysis—Slides were analyzed using fluorescent microscopy.

Results

Figure 2:
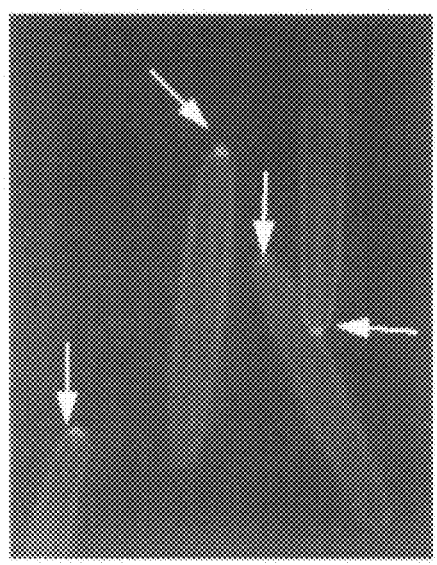
FIG. 2 is an image captured by microscopy of the stinging capsules stained with the ionic fluorescent dye fluoresceine. The arrows point to the specific staining of the fluoreceine at the tip of the capsule from where the tubule is released.

As can be seen from FIGS. 1A and 1B and FIG. 2, specific labeling of the opening tip can be seen using ionic micelles or the ionic fluorescent dye floureceine. This specific labeling was not detected using cationic micelles.

Conclusion

Capsules have asymmetric characteristics as they are positively charged at their opening tip.

Example 2

Insulin Delivery

The potential of the stinging capsule patch to deliver an agent (insulin) into the blood stream was tested with aiptasia capsules.

Materials and Methods

Materials—Commercial Insulin—Humolin of EliLilly was tested. Unless otherwise noted, all chemicals were purchased from Sigma (Aldrich).

Animals—6-9 week old nude mice each weighing 20-30 gr were used.

Insulin Delivery—Mice were topically applied with the aiptasia stinging capsule gel and Humolin. A few microlitres of blood were drawn from the tail tip prior to insulin application (time 0) and thirty minutes, sixty minutes and ninety minutes following gel activation. Blood glucose concentration was measured using a human glucometer.

In parallel, and as a positive control, mice were subcutaneously injected with Humolin.

Results

Figure 3:
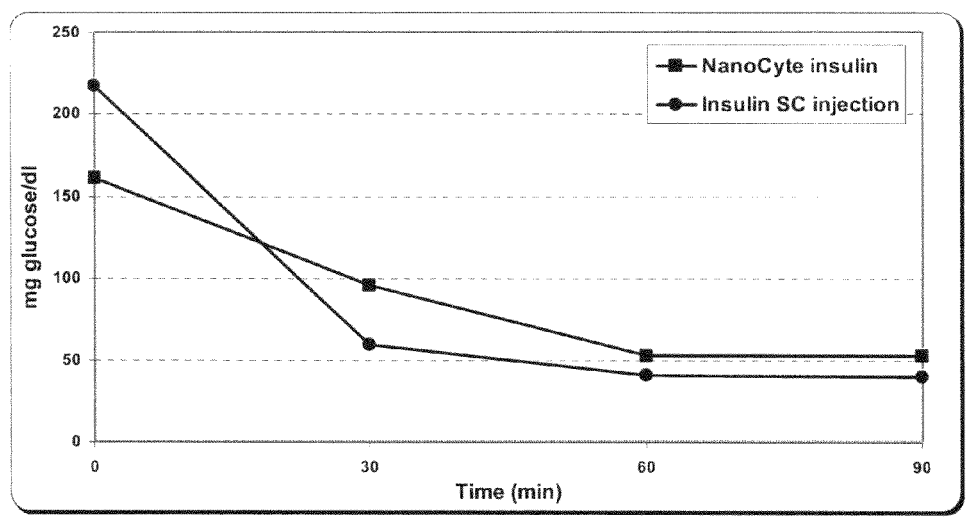
FIG. 3 is a graphical presentation comparing the effect of subcutaneous insulin administration (SC injection, indicated by circles) and Aiptasia diaphana capsule facilitated insulin administration (Nanocyte Insulin, indicated by squares) on blood glucose levels in nude mice.

As can be seen from FIG. 3, capsule topical application delivers insulin in a similar manner as subcutaneous injection since glucose regulation followed a similar time scale in each.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of delivering an active agent into and/or through a tissue, the method comprising:
    (a) preconditioning the tissue by:
        (i) administering onto the tissue a composition including at least one stinging capsule/cell, wherein said composition further comprises an orientation and proximity agent selected for positioning said at least one stinging capsule/cell in intimate proximity with said tissue; and orientating said at least one stinging capsule/cell such that the opening tip of said stinging capsule substantially faces said tissue, wherein said orientation and proximity agent is selected from the group consisting of a negatively charged agent, an adhesive agent and an amphoteric agent; and
        (ii) discharging said at least one stinging capsule/cell to thereby deliver a tubule of said at least one stinging capsule/cell into the tissue, thereby producing tissue having said tubule embedded therein and being devoid of the active agent; and subsequently
    (b) applying the active agent onto said tissue having tubules embedded therein, thereby initiating diffusion of the active agent into the tissue through a channel formed by said tubule.

2. The method of claim 1, wherein said at least one stinging cell is an isolated stinging cell.

3. The method of claim 1, wherein said discharging is effected by hydration or a change in pH.

4. The method of claim 1, wherein said orientation and proximity agent is selected from the group consisting of an anionic polymer, a polysaccharide polyethylene oxide, polyvinyl alcohol, carbomer, lectin and bacterial fimbrin.

5. The method of claim 1, wherein said at least one stinging capsule/cell is administered onto said tissue using an applicator.

6. The method of claim 5, wherein said applicator is selected from the group consisting of a patch, a foil, a plaster and a pad.

* * * * *